United States Patent [19]

Chang

[11] Patent Number: 4,552,585
[45] Date of Patent: Nov. 12, 1985

[54] HERBICIDAL 2-(AMINOPHENYL)METHYL DERIVATIVES OF 3-ISOXAZOLIDINONES OR 3-OXAZINONES

[75] Inventor: Jun H. Chang, Princeton Junction, N.J.

[73] Assignee: FMC Corporation, Philadelphia, Pa.

[21] Appl. No.: 657,848

[22] Filed: Oct. 4, 1984

[51] Int. Cl.$^4$ .................. A01N 43/72; A01N 43/74; C07D 261/04; C07D 265/02

[52] U.S. Cl. .......................... 71/88; 544/63; 548/241; 548/243

[58] Field of Search .............. 544/63; 548/241, 243; 71/88

[56] References Cited

U.S. PATENT DOCUMENTS 4,174,958 11/1979 Pilgram .................. 71/88
4,405,357 9/1983 Chang .................. 71/88

Primary Examiner—Richard L. Raymond
Attorney, Agent, or Firm—Robert L. Anderson; H. Robinson Ertelt; William Schmonsees

[57] ABSTRACT

Compounds of the formula,

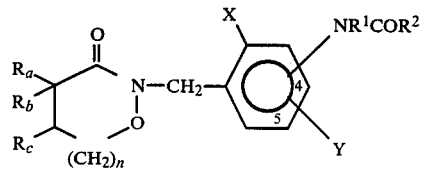

formulations thereof, and their use as herbicides are disclosed and exemplified.

10 Claims, No Drawings

HERBICIDAL 2-(AMINOPHENYL)METHYL DERIVATIVES OF 3-ISOXAZOLIDINONES OR 3-OXAZINONES

The present invention relates to herbicidal 2-(amidophenyl)methyl derivatives of 3-isoxazolidinones and 3-oxazinones, herbicidal compositions of such compounds, and use of such compounds as herbicides.

Certain 3-isoxazolidinones are known to have herbicidal activity. For example, herbicidal activity of certain 2-(phenylmethyl)-3-isoxazolidinones, in which the phenyl ring is substituted with one or more halogen atoms, methoxy, or cyano, have been reported in U.S. Pat. No. 4,405,357.

The present invention provides herbicidal compounds and intermediates therefor which are amidophenyl-3-isoxazolidinone or 3-oxazinone compounds of formula I

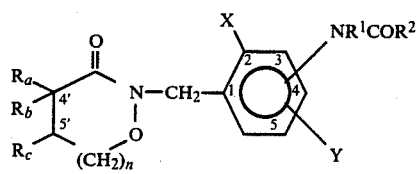

in which:

n is zero or one, $NR^1COR^2$ is in one of positions 4 and 5;

$R_a$ is hydrogen or alkyl of 1 to 3 carbon atoms, preferably methyl;

$R_b$ is hydrogen, alkyl of 1 to 3 carbon atoms, or methylthio;

$R_c$ is hydrogen, alkyl of 1 to 3 carbon atoms, or phenyl; or $R_a$, $R_b$ and $R_c$ taken with carbon atoms at positions 4' and 5' form a benzene ring;

X is hydrogen or halogen;

Y is hydrogen or halogen at the other of positions 4 and 5;

$R^1$ is hydrogen, or alkyl of 1 to 4 carbon atoms;

$R^2$ is alkyl of 1 to 6 carbon atoms, haloalkyl of 2 to 4 carbon atoms, cyclopropyl, methylcyclopropyl, benzyl, alkoxy of 1 or 2 carbon atoms, t-butyloxy when $R^1$ or Y is other than hydrogen, haloalkoxy of 3 or 4 carbon atoms, or $-NR^3R^4$;

$R^3$ is methyl; and $R^4$ is hydrogen, methyl, methoxy or benzyl.

The invention may be illustrated more specifically by reference to compounds of formula I as described above in which:

A. when n is zero $R_a$ and $R_b$ are both hydrogen or alkyl of 1 to 3 carbon atoms, preferably methyl;

$R_c$ is hydrogen, alkyl of 1 to 3 carbon atoms, preferably methyl, or phenyl;

X, $R^1$, $R^2$, $R^3$, and $R^4$ and Y are as defined above, or

B. when n is 1, $R_a$ is alkyl of 1 to 3 carbon atoms, preferably methyl;

$R_b$ is alkyl of 1 to 3 carbon atoms, preferably methyl, or methylthio;

$R_c$ is hydrogen; or $R_a$, $R_b$, and $R_c$, together with carbon atoms at positions 4' and 5' form a benzene ring;

$R^1$ is hydrogen;

$R^2$ is $NR^3R^4$;

$R^3$ is methyl; and $R^4$ is methyl or methoxy.

The compounds of this invention are particularly effective as herbicides for control of undesired vegetation in agricultural crops such as soybeans, wheat and corn. Particularly effective are those compounds of formula I in which:

n is zero, $NR^1COR^2$ is at position 4, $R_a$ and $R_b$ are both methyl, $R_c$ is hydrogen, X is chloro or fluoro, Y is hydrogen or 5-fluoro, $R^1$ is hydrogen and $R^2$ is $N(CH_3)R^5$ in which $R^5$ is methyl or methoxy.

In a second aspect the invention also comprises certain novel intermediates for preparation of the herbicidal compounds of the invention. The novel intermediates of this invention are compounds of the formula II:

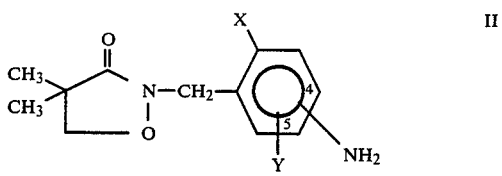

in which X is halogen, Y is hydrogen, chloro, or fluoro, one of Y and $NH_2$ is in position 5 and the other of Y and $NH_2$ is in position 4.

Preparation of the compounds of the invention is illustrated in the examples set forth below. The compound numbers set forth in the examples indicate the structure shown in Table 1.

EXAMPLE 1

Synthesis of 2-[2-chloro-4-(methoxycarbonylamino)phenyl]methyl-4,4-dimethyl-3-isoxazolidinone (Compound 14)

Step A Synthesis of methyl(3-chloro-4-methylphenyl)carbamate as an intermediate To a stirred solution of 10.0 grams (0.071 mole) of 3-chloro-4-methylaniline in 100 ml of chloroform was added 16.7 grams (0.212 mole) of pyridine. Methyl chloroformate, 8.0 grams (0.085 mole), was then added dropwise during a 20 minute period. During the addition the reaction mixture temperature was held between 25°–30° C. with external cooling. Upon completion of addition the reaction mixture was stirred at ambient temperature for 16 hours. The reaction mixture was washed into a separatory funnel with 50 ml of chloroform; and the solution was washed with two 100 ml portions of water and 100 ml of aqueous 5% hydrochloric acid. The organic layer was dried with magnesium sulfate and filtered. The filtrate was concentrated under reduced pressure to a waxy solid residue. The residue was recrystallized from hexane/ethyl acetate to give 10.9 grams of methyl(3-chloro-4-methylphenyl)carbamate; m.p. 80°–81.5° C.

Analysis calcd for $C_9H_{10}ClNO_2$: C 54.14; H 5.05; N 7.02; Found: C 53.90; H 5.03; N 7.02.

Step B Synthesis of methyl(4-bromomethyl-3-chlorophenyl)carbamate as an intermediate To a stirred solution of 10.9 grams (0.055 mole) of methyl(3-chloro-4-methylphenyl)carbamate in 110 ml of carbon tetrachloride, under an argon atmosphere, was added 9.7 grams (0.055 mole) of N-bromosuccinimide. The reaction mixture was irradiated with a 250 watt brooder lamp, placed at such a distance as to cause a gentle reflux. The reflux was continued for 20 hours. The reaction mixture was cooled and a solid collected by filtration. The solid was slurried with water and the insoluble material collected by filtration. The filter cake was dried to give 8.5 grams of methyl(4-bromomethyl-3-chlorophenyl)carbamate; m.p. 128°–131° C.

Analysis calcd for $C_9H_9BrClNO_2$: C 38.80; H 3.26; N 5.03; Found: C 39.35; H 3.50; N 5.15.

Step C Synthesis of 2-[2-chloro-4-(methoxycarbonylamino)phenyl]methyl-4,4-dimethyl-3-isoxazolidinone To a stirred suspension of 2.4 grams (0.017 mole) of potassium carbonate and 0.1 gram (0.02 eq.) of 1,4,7,10,13,16-hexaoxacyclooctadecane in 60 ml of acetonitrile, at ambient temperature, was added dropwise a mixture of 2.0 grams (0.017 mole) of 4,4-dimethyl-3-isoxazolidinone and 4.8 grams (0.017 mole) of methyl(4-bromomethyl-3-chlorophenyl)carbamate in 30 ml of acetonitrile. The complete addition required 30 minutes, after which the reaction mixture stirred for 16 hours. The reaction mixture was filtered to collect a solid. The solid was slurried with 300 ml of water and the insoluble material collected by filtration. The filter cake was recrystallized from hexane/ethyl acetate to give 2.4 grams of 2-[2-chloro-4-(methyloxycarbonylamino)phenyl]methyl-4,4-dimethyl-3-isoxazolidinone; m.p. 165°–167° C. (Compound 14)

Analysis calcd for $C_{14}H_{17}ClN_2O_4$: C 53.76; H 5.48; N 8.96; Found: C 53.69; H 5.52; N 8.72.

EXAMPLE 2

Synthesis of 2-[2-chloro-4-(methylaminocarbonylamino)phenyl]-methyl-4,4-dimethyl-3-isoxazolidinone (Compound 24)

Step A Synthesis of 2-[2-chloro-4-(ethoxycarbonylamino)phenyl]methyl-4,4-dimethyl-3-isoxazolidinone (Compound 15)

This compound was prepared in the manner of Example 1, Step C, using 17.2 grams (0.06 mole) of ethyl(4-bromomethyl-3-chlorophenyl)carbamate, 6.8 grams (0.06 mole) of 4,4-dimethyl-3-isoxazolidinone, 8.2 grams (0.06 mole) of potassium carbonate, and 0.32 gram (0.001 mole) of 1,4,7,10,13,16-hexaoxacyclooctadecane in acetonitrile. The yield of 2-[2-chloro-4-(ethoxycarbonylamino)phenyl]methyl-4,4-dimethyl-3-isoxazolidinone was 12.0 grams as a solid; m.p. 162°–164° C.

Analysis calcd for $C_{15}H_{19}ClN_2O_4$: C 55.13; H 5.86; N 8.57; Found: C 55.04; H 5.81; N 8.50.

Step B Synthesis of 2-(4-amino-2-chlorophenyl)methyl-4,4-dimethyl-3-isoxazolidinone To a stirred suspension of 8.4 grams (0.026 mole) of 2-[2-chloro-4-(ethoxycarbonylamino)phenyl]methyl-4,4-dimethyl-3-isoxazolidinone in 100 ml of chloroform, under an argon atmosphere and at ambient temperature, was carefully added dropwise 6.0 grams (0.03 mole) of iodotrimethylsilane. Upon completion of addition the reaction mixture was warmed to 60° C. where it stirred for 16 hours. Five ml of methanolic 2N hydrochloric acid was added to the reaction mixture. The solution was stirred for 10 minutes, then concentrated under reduced pressure to a residual solid. The solid was triturated in 25 ml of water. The water/solid mixture was neutralized with aqueous saturated sodium bicarbonate solution. The solid was collected by filtration to give 2-(4-amino-2-chlorophenyl)methyl-4,4-dimethyl-3-isoxazolidinone; m.p. 106°–108° C.

Analysis calcd for $C_{12}H_{13}ClN_3O_2$: C 57.04; H 5.19; N 11.09; Found: C 57.13; H 5.45, N 10.65.

Step C Synthesis of 2-[2-chloro-4-(methylaminocarbonylamino)phenyl]-methyl-4,4-dimethyl-3-isoxazolidinone (Compound 19)

To a stirred solution of 1.4 grams (0.06 mole) of 2-(4-amino-2-chlorophenyl)methyl-4,4-dimethyl-3-isoxazolidinone in 25 ml of chloroform, under an argon atmosphere, was added dropwise 5 ml of methyl isocyanate. Upon completion of addition the reaction mixture stirred at ambient temperature for 16 hours. The reaction mixture was concentrated under reduced pressure to a residual solid. The solid was recrystallized from ethanol to give 1.4 grams of 2-[2-chloro-4-(methylaminocarbonylamino)phenyl]methyl-4,4-dimethyl-3-isoxazolidinone; m.p. 227°–229° C.

Analysis calcd for $C_{14}H_{18}ClN_3O_3$: C 53.94; H 5.82; N 13.48; Found: C 54.03; H 6.09; N 13.29.

EXAMPLE 3

Synthesis of 2-(2-chloro-4-[(N-methoxy-N-methylamino)carbonylamino]phenyl)methyl-4,4-dimethyl-3-isoxazolidinone (Compound 21)

Step A Synthesis of 2-(2-chloro-4-isocyanatophenyl)methyl-4,4-dimethyl-3-isoxazolidinone as an intermediate.

To a stirred solution of 7.9 grams (0.08 mole) of phosgene in toluene was added dropwise a solution of 5.0 grams (0.02 mole) of 2-(4-amino-2-chlorophenyl)methyl-4,4-dimethyl-3-isoxazolidinone in tetrahydrofuran. Upon completion of addition the reaction mixture was warmed to 80° C. where it stirred for 3 hours. The reaction mixture was concentrated under reduced pressure to give 5.6 grams of 2-(2-chloro-4-isocyanatophenyl)methyl-4,4-dimethyl-3-isoxazolidinone as a residual solid.

Step B Synthesis of 2-(2-chloro-4-[(N-methoxy-N-methylamino)carbonylamino]phenyl)methyl-4,4-dimethyl-3-isoxazolidinone (Compound 21)

A stirred solution of 2.0 grams (0.02 mole) of O,N-dimethylhydroxylamine hydrochloride in 25 ml of dry tetrahydrofuran was cooled to −30° C. and 2.0 grams (0.02 mole) of triethylamine in 25 ml of dry tetrahydrofuran was added. The reaction mixture was stirred for 20 minutes and 5.6 grams (0.02 mole) of 2-(2-chloro-4-isocyanatophenyl)methyl-4,4-dimethyl-3-isoxazolidinone in 75 ml of dry tetrahydrofuran was added dropwise. The reaction mixture temperature was maintained at −30° C. throughout the addition. Upon completion of addition the reaction mixture was allowed to warm to ambient temperature as it stirred for 16 hours. The reaction mixture was heated under reflux for one hour then cooled to ambient temperature. The reaction mixture was placed in a separatory funnel and 20 ml of diethyl ether was added. The mixture was washed with three portions of 50 ml each of water, then dried with sodium sulfate. The mixture was filtered and the filtrate concentrated under reduced pressure to a residual oil. The oil was crystallized from heptane/ethyl acetate to give 4.2 grams of 2-(2-chloro-4-[(N-methoxy-N- methylamino)carbonylamino]phenyl)methyl-4,4-dimethyl-3-isoxazolidinone; m.p. 93°–95° C.

Analysis calcd for $C_{15}H_{20}ClN_3O_4$: C 52.71; H 5.90; N 12.29; Found: C 52.65; H 5.99; N 12.00.

EXAMPLE 4

Synthesis of 2-[2-chloro-4-(dimethylaminocarbonylamino)phenyl]-methyl-4,4-dimethyl-3-isoxazolidinone (Compound 20)

Step A Synthesis of 1,1-dimethylethyl (3-chloro-4-methylphenyl)carbamate as an intermediate To a stirred solution of 25.0 grams (0.1 mole) of 3-chloro-4-methylaniline in 50 ml of methanol was added dropwise a solution of 25.4 grams (0.11 mole) of di-tert-butyl dicarbonate in 50 ml of methanol. The addition caused the reaction mixture temperature to rise to 35° C. Upon completion of addition the reaction mixture stirred at ambient temperature for 16 hours. The reaction mixture was concentrated under reduced pressure to a residual solid. The solid was recrystallized from heptane. A small amount of solid, m.p. 103°–104° C., was collected by filtration. The filtrate was placed in a freezer for 60 hours. A white precipitate was collected by filtration. The mother liquor was concentrated under reduced pressure to a residual solid. The solid precipitate and the residual solid were combined and subjected to column chromatography on silica gel. Elution was accomplished with 1:9—ethyl acetate:heptane. The appropriate fractions were combined and concentrated under reduced pressure to give a residual solid; m.p. 103°–104° C. Both solids, m.p. 103°–104° C. were combined to give 22.2 grams of 1,1-dimethylethyl(3-chloro-4-methylphenyl)carbamate.

Analysis calcd for $C_{12}H_{16}ClNO_2$: C 59.63; H 6.67; N 5.79; Found: C 59.33; H 6.40; N 5.82.

Step B Synthesis of 1,1-dimethylethyl(4-bromomethyl-3-chlorophenyl)carbamate as an intermediate This compound was prepared in the manner of Example 1, Step B, using 21.6 grams (0.089 mole) of 1,1-dimethylethyl(3-chloro-4-methylphenyl)carbamate, and 15.8 grams (0.089 mole) of N-bromosuccinimide in 200 ml of carbon tetrachloride. The yield of 1,1-dimethylethyl(4-bromomethyl-3-chlorophenyl)carbamate was 10.5 grams; m.p. 225° C.

Analysis calcd for $C_{12}H_{15}BrClNO_2$: C 44.95; H 4.72; N 4.37; Found: C 45.01; H 4.87; N 4.49.

Step C Synthesis of 2-[2-chloro-4-(1,1-dimethylethoxycarbonylamino)-phenyl]methyl-4,4-dimethyl-3-isoxazolidinone This compound was prepared in the manner of Example 1, Step C using 8.1 grams (0.025 mole) of 1,1-dimethylethyl(4-bromomethyl-3-chlorophenyl)carbamate, 2.9 grams (0.025 mole) of 4,4-dimethyl-3-isoxazolidinone, 3.5 grams (0.025 mole) of potassium carbonate, and 0.13 gram (0.005 mole) of 1,4,7,10,13,16-hexaoxacyclooctadecane in 75 ml of acetonitrile. The yield of 2-[2-chloro-4-(1,1-dimethylethoxycarbonylamino)-phenyl]methyl-4,4-dimethyl-3-isoxazolidinone was 5.8 grams; m.p. 124°–126° C.

Analysis calcd for $C_{17}H_{23}ClN_2O_4$: C 57.54; H 6.53; N 7.89; Found: C 57.80; H 6.36; N 7.76.

Step D Synthesis of 2-(4-amino-2-chlorophenyl)methyl-4,4-dimethyl-3-isoxazolidinone To a stirred solution of 2.0 grams (0.006 mole) of 2-[2-chloro-4-(1,1-dimethylethoxycarbonylamino)-phenyl]methyl-4,4-dimethyl-3-isoxazolidinone in 10 ml of methylene chloride was added dropwise a solution of 10 ml of trifluoroacetic acid in 10 ml of methylene chloride. Upon completion of addition the reaction mixture stirred at ambient temperature for 3.5 hours. The reaction mixture was slurried with 50 ml of water and neutralized with a saturated aqueous solution of potassium carbonate. A solid precipitate was collected by filtration to give 1.3 grams of 2-(4-amino-2-chlorophenyl)-methyl-4,4-dimethyl-3-isoxazolidinone; m.p. 106°–108° C.

Step E Synthesis of 2-[2-chloro-4-(dimethylaminocarbonylamino)phenyl]-methyl-4,4-dimethyl-3-isoxazolidinone (Compound 20)

Under an argon atmosphere, a stirred solution of 1.4 grams (0.009 mole) of phosgene iminium chloride in 50 ml of dry methylene chloride was cooled to 0° to −5° C. and 2.0 grams (0.008 mole) of 2-(4-amino-2-chlorophenyl)methyl-4,4-dimethyl-3-isoxazolidinone was added. Upon completion of addition the reaction mixture was warmed to reflux where it stirred for 3 hours. The reaction mixture was cooled and concentrated under reduced pressure to a solid residue. The residual solid was stirred with 50 ml of aqueous 5% hydrochloric acid, then extracted with three 50 ml portions of methylene chloride. The combined extracts were dried with magnesium sulfate and filtered. The filtrate was concentrated under reduced pressure to a residual oil. The oil solidified and was recrystallized from hexane/ethyl acetate to give 1.4 grams of 2-[2-chloro-4-(dimethylaminocarbonylamino)phenyl]methyl-4,4-dimethyl-3-isoxazolidinone; m.p. 145°–147° C.

Analysis calcd for $C_{15}H_{20}ClN_3O_3$: C 55.30; H 6.19; N 12.90; Found: C 54.70; H 5.98; N 12.56.

EXAMPLE 5

Synthesis of 2-[2-chloro-4-(cyclopropylcarbonylamino)phenyl]-methyl-4,4-dimethyl-3-isoxazolidinone (Compound 12)

To a stirred solution of 3.0 grams (0.012 mole) of 2-(4-amino-2-chlorophenyl)methyl-4,4-dimethyl-3-isoxazolidinone and 1.2 grams (0.012 mole) of triethylamine in 30 ml of tetrahydrofuran was added dropwise 1.4 grams (0.013 mole) of cyclopropanecarboxylic acid chloride in 20 ml of tetrahydrofuran. During the addition the reaction mixture was cooled in an ice-water bath. Upon completion of addition the reaction mixture stirred for 16 hours; then was concentrated under reduced pressure to a residual solid. The solid was dissolved in 250 ml of methylene chloride. The solid was washed with water, which caused the precipitation of a solid that was insoluble in the liquid phases. The solid was removed by filtration. The organic phase was separated and washed with three 100 ml portions of water. The organic phase was dried with magnesium sulfate and filtered. The filtrate was concentrated under reduced pressure to a residual solid. Both solids collected were subjected to thin layer chromatography and were determined to be the same material. The solids were combined and recrystallized from ethyl acetate/acetonitrile to give 2.5 grams of 2-[2-chloro-4-(cyclopropylcarbonylamino)phenyl]methyl-4,4-dimethyl-3-isoxazolidinone; m.p. 191°–193° C.

Analysis calcd for $C_{16}H_{19}ClN_2O_3$: C 59.53; H 5.93; N 8.68; Found: C 59.23; H 6.22; N 8.41.

EXAMPLE 6

Synthesis of 2-(2-chloro-4-[(N-methoxy-N-methylamino)carbonylamino]phenyl)methyl-5,6-dihydro-4,4-dimethyl-2H-1,2-oxazin-3(4H)-one (Compound 29)

Part A Synthesis of 2-chloro-4-[(N-methoxy-N-methylamino)carbonylamino]phenylmethyl bromide as an intermediate To a stirred solution of 100.0 grams (0.597 mole) of 3-chloro-4-methylphenylisocyanate in 1000 ml of carbon tetrachloride, under an argon atmosphere were added 116.8 grams (0.656 mole) of N-bromosuccinimide and 5.0 grams (0.021 mole) of benzoyl peroxide. The reaction mixture was warmed to reflux where it stirred for 4 hours; then it was allowed to cool to ambient temperature as it stood for 16 hours. The mixture was filtered and the filtrate concentrated under reduced pressure to give 147.1 grams of 4-bromomethyl-3-chlorophenylisocyanate as a residual oil. The oil was used without further purification.

A stirred solution of 58.3 grams (0.597 mole) of O,N-dimethylhydroxylamine hydrochloride in 400 ml of diethyl ether was cooled to 0° C. and a slurry of 50.2 grams (0.597 mole) of sodium bicarbonate in 50 ml of water was added. Upon completion of addition the reaction mixture stirred at 0° C. for one hour, then a solution of 147.2 grams (0.597 mole) of 4-bromomethyl-3-chlorophenylisocyanate in 100 ml of diethyl ether was added. During the addition, additional diethyl ether was added to the reaction mixture to promote stirring. Upon completion of addition the reaction mixture was stirred for an additional one hour, then was filtered. The filtrate was dried with magnesium sulfate and refiltered. The filtrate was concentrated under reduced pressure to a solid residue. The solid was triturated with ethanol to remove a yellow color. The solid was collected by filtration to give 51.5 grams of 2-chloro-4-[(N-methoxy-N-methylamino)carbonylamino]phenylmethyl bromide.

Part B Synthesis of 5,6-dihydro-4,4-dimethyl-2H-1,2-oxazin-3(4H)-one as an intermediate The reaction vessel was dried and, under an argon atmosphere, 75.9 grams (0.75 mole) of diisopropylamine and 450 ml of tetrahydrofuran was added. The stirred solution was cooled to −70° C. and 48.0 grams (0.75 mole-484 ml of 1.5 molar in hexane) of n-butyl lithium was added. Upon completion of addition the reaction mixture stirred for 20 minutes and, at −70° C., 68.9 grams (0.675 mole) of methyl isobutyrate was added dropwise. Upon completion of addition the reaction mixture stirred for an additional 20 minutes and, at −70° C., 108.0 grams (0.75 mole) of 1-bromo-2-chloroethane was added dropwise. The reaction mixture was allowed to warm to ambient temperature where it stirred for 16 hours. After this time 500 ml of water, then 85 ml of concentrated hydrochloric acid, were added dropwise to the reaction mixture. Upon completion of addition the reaction mixture stirred for an additional five minutes. The organic layer was separated and washed with 150 ml of aqueous 10% hydrochloric acid. The combined aqueous layers were washed with 150 ml of methylene chloride. The combined organic layers were dried with magnesium sulfate and filtered. The filtrate was concentrated under reduced pressure to a residual oil. The oil was distilled under reduced pressure to give 84.2 grams of methyl 4-chloro-2,2-dimethylbutanoate; b.p. 80°–84° C./15 mm.

To a stirred solution of 83.2 grams (0.51 mole) of N-hydroxyphthalimide in 500 ml of dimethyl sulfoxide was added 41.8 grams (0.51 mole) of sodium acetate. Upon completion of addition the reaction mixture was stirred for one hour at ambient temperature. After this time 84.2 grams (0.51 mole) of methyl 4-chloro-2,2-dimethylbutanoate was added dropwise. The reaction mixture was then heated to 100° C. where it stirred for 16 hours. The reaction mixture was cooled and 300 ml of water and 1000 ml of ethyl acetate were added. The mixture was shaken and the organic layer separated. The organic layer was washed with three 200 ml portions of water. The organic layer was dried with magnesium sulfate and filtered. The filtrate was concentrated under reduced pressure to a residual oil. The oil was subjected to column chromatography on silica gel. Elution was accomplished with 1:3 ethyl acetate:heptane. The appropriate fractions were combined and concentrated under reduced pressure to a residual oil. The oil was dissolved in 500 ml of diethyl ether and washed with two 100 ml portions of aqueous 1N sodium hydroxide. The ether layer was concentrated under reduced pressure to give 90.3 grams of methyl 2,2-dimethyl-4-(phthalimidooxy)butanoate as an oil.

To a stirred solution of 85.3 grams (0.30 mole) of methyl 2,2-dimethyl-4-(phthalimidooxy)butanoate in 500 ml of methanol was added dropwise a solution of 30.0 grams (0.60 mole) of hydrazine hydrate in 100 ml of methanol. Upon completion of addition the reaction mixture stirred at ambient temperature for 3 hours. The resultant precipitate was removed by filtration. The filtrate was acidified with concentrated hydrochloric acid. The mixture was stirred for 20 minutes and filtered. The filtrate was concentrated under reduced pressure to a residual semi-solid. The semi-solid was dissolved in hot ethyl acetate. A small amount of insoluble material was removed by filtration. The filtrate was cooled and a small amount of additional solid was collected by filtration. The filtrate was cooled further in a freezer and the resultant precipitate was collected by filtration. The yield of methyl 4-aminooxy-2,2-dimethylbutanoate hydrochloride was 38.0 grams.

A solution of 38.0 grams (0.19 mole) of methyl 4-aminooxy-2,2-dimethylbutanoate hydrochloride in 100 ml of pyridine was heated to 60° C. where it stirred for 16 hours. The reaction mixture was concentrated under reduced pressure to a residual oil. The oil was slurried in 500 ml of water and the mixture extracted with three 100 ml portions of methylene chloride. The combined extracts were washed with two 100 ml portions of aqueous 10% hydrochloric acid. The organic layer was dried with magnesium sulfate and filtered. The filtrate was concentrated under reduced pressure to give 13.0 grams of solid. The aqueous layer was saturated with sodium chloride and re-extracted with three 75 ml portions of methylene chloride. The combined extracts were dried with magnesium sulfate and filtered. The filtrate was concentrated under reduced pressure to give an additional 2.0 grams of solid. The solids were combined to give 15.0 grams of 5,6-dihydro-4,4-dimethyl-2H-1,2-oxazin-3(4H)-one; m.p. 115°–119° C.

Analysis calcd for $C_6H_{11}NO_2$: C 55.79; H 8.59; N 10.84; Found: C 55.55; H 8.30; N 10.77.

Part C Synthesis of 2-(2-chloro-4-[(N-methoxy-N-methylamino)carbonylamino]phenyl)methyl-5,6-dihydro-4,4-dimethyl-2H-1,2-oxazin-3(4H)-one (Compound 29)

This compound was prepared in the manner of Example 1, Step C; using 1.3 grams (0.01 mole) of 5,6-dihydro-4,4-dimethyl-2H-1,2-oxazin-3(4H)-one, 3.1 grams (0.01 mole) of 2-chloro-4-[(N-methoxy-N-methylamino)carbonylamino]phenylmethyl bromide, 1.4 grams (0.01 mole) of potassium bromide and 0.1 gram (0.0004 mole) of 1,4,7,10,13,16-hexaoxacyclooctadecane in 50 ml of acetonitrile. The yield of 2-(2-chloro-4-[(N-methoxy-N-methylamino)carbonylamino]-phenyl)methyl-5,6-dihydro-4,4-dimethyl-1H-1,2,-oxazin-3(4H)-one was 2.9 grams; m.p. 116°–118° C.

Analysis calcd for $C_{16}H_{22}ClN_3O_4$: C 54.01; H 6.23; N 11.81; Found: C 53.78; H 6.25; N 11.77.

EXAMPLE 7

Synthesis of 2-(2-chloro-4-[(N-methoxy-N-methylamino)carbonylamino]phenyl)methyl-5,6-dihydro-4-methyl-4-methylthio-2H-1,2-oxazin-3(4H)-one (Compound 31)

Step A Synthesis of alpha-methyl-alpha-methylthio-gamma-butyrolactone as an intermediate A stirred solution of 309.0 grams (3.06 moles) of diisopropylamine in 1100 ml of tetrahydrofuran was cooled to −78° C. and 195.9 grams (3.06 moles–1800 ml, 1.7 Molar in hexane) of n-butyl lithium was added slowly. Upon completion of addition the reaction mixture was stirred for 30 minutes and a solution of 278.0 grams (2.78 moles) of alpha-methyl-gamma-butyrolactone in 360 ml of tetrahydrofuran was added slowly. Upon completion of addition the reaction mixture was stirred for 30 minutes and a solution of 392.8 grams (4.17 moles) of dimethyl disulfide in 360 ml of tetrahydrofuran was added slowly. Upon completion of addition the reaction mixture was allowed to warm to ambient temperature during a one hour period. The reaction mixture was stirred with 1600 ml of aqueous 5% hydrochloric acid for several minutes then 2000 ml of ethyl acetate was added. The organic layer was separated and washed with 800 ml of aqueous 10% hydrochloric acid, then with 800 ml of an aqueous solution saturated with sodium bicarbonate. The organic layer was dried with magnesium sulfate and filtered. The filtrate was concentrated under reduced pressure to a residual oil. The oil was distilled to give 234.6 grams of alpha-methyl-alpha-methyl-thio-gamma-butyrolactone; b.p. 104°–105° C./8 mm.

Step B Synthesis of ethyl 4-bromo-2-methyl-2-methylthiobutanoate as an intermediate A stirred solution of 234.0 grams (1.59 moles) of alpha-methyl-alpha-methylthio-gamma-butyrolactone in 1000 ml of ethanol was cooled in an ice-water bath and 680.4 g (8.41 moles) of gaseous hydrogen bromide was bubbled in. Upon completion of addition the reaction mixture was allowed to warm to ambient temperature where it stirred for 16 hours. An additional 453.6 grams (5.61 moles) of gaseous hydrogen bromide was bubbled in. Upon completion of addition the reaction mixture stirred at ambient temperature for an additional 64 hours. GLC analysis of the reaction mixture after this time indicated the reaction was 81% complete. An additional 500 ml of ethanol was added and the reaction mixture stirred for 16 hours. The reaction mixture was concentrated under reduced pressure to remove most of the ethanol. The concentrate was taken up in 400 ml of methylene chloride and the mixture washed with three 100 ml portions of water. The organic layer was dried with magnesium sulfate and filtered. The filtrate was concentrated under reduced pressure to a residual oil. The oil was distilled under reduced pressure giving a Vigreux column to give 280.5 grams of a mixture of ethyl 4-bromo-2-methyl-2-methylthiobutanoate and starting lactone; b.p. 114°–125° C./8 mm.

A stirred solution of the ester/lactone mixture in 500 ml of ethanol was cooled in an ice-water bath and saturated with gaseous hydrogen bromide. The reaction mixture was stirred at ambient temperature for three days. The mixture was dissolved in 500 ml of methylene chloride and washed with three portions of 100 ml each of water. The organic layer was dried with magnesium sulfate and filtered. The filtrate was concentrated under reduced pressure to a residual oil. The oil was distilled under reduced pressure to give 168.0 grams of ethyl 4-bromo-2-methyl-2-methylthiobutanoate that was 97% pure by GLC analysis.

Step C Synthesis of ethyl 2-methyl-2-methylthio-4-(phthalimidooxy)butanoate as an intermediate This compound was prepared in the manner of Example 6, Step B, using 150.0 grams (0.588 mole) of ethyl 4-bromo-2-methyl-2-methylthiobutanoate, 95.9 grams (0.588 mole) of N-hydroxyphthalimide and 53.0 grams (0.647 mole) of sodium acetate in 1000 ml of dimethyl sulfoxide. The yield of ethyl 1-methyl-2-methylthio-4-(phthalimidooxy)butanoate was 93.0 grams as an oil.

Step D Synthesis of ethyl 4-aminooxy-2-methyl-2-methylthiobutanoate hydrochloride as an intermediate This compound was prepared in the manner of Example 6, Part 2, Step C, using 93.0 grams (0.276 mole) of ethyl 2-methyl-2-methylthio-4-(phthalimidooxy)-butanoate and 23.5 grams (0.469 mole) of hydrazine hydrate in 800 ml of ethanol. The yield of ethyl 4-aminooxy-2-methyl-2-methylthiobutanoate was 53.3 grams as an oil.

Step E Synthesis of 5,6-dihydro-4-methyl-4-methylthio-2H-1,2-oxazin-3(4H)-one as an intermediate This compound was prepared in the manner of Example 6, Step D, using 53.0 grams (0.213 mole) of ethyl 4-aminooxy-2-methyl-2-methylthiobutanoate in 100 ml of pyridine. A residual solid was recrystallized from ethyl acetate/heptane to give 11.2 grams of 5,6-dihydro-4-methyl-4-methylthio-2H-1,2-oxazin-3(4H)-ones; m.p. 81°–84° C.

Step F Synthesis of 2-(2-chloro-4-[(N-methoxy-N-methylamino)carbonylamino]phenyl)methyl-5,6-dihydro-4-methyl-4-methylthio-2H-1,2-oxazin-3(4H)-one (Compound 31)

This compound was prepared in the manner of Example 1, Step C, using 1.0 gram (0.006 mole) of 5,6-dihydro-4-methyl-4-methylthio-2H-1,2-oxazin-3(4H)-one, 1.9 grams (0.006 mole) of 2-chloro-4-[(N-methoxy-N-methylamino)carbonylamino]phenylmethyl bromide (prepared in Example 6, Part 1, Step B), 0.86 gram (0.006 mole) of potassium carbonate, and 0.03 gram of 1,4,7,10-13,16-hexaoxacyclooctadecane in 75 ml of acetonitrile. The yield of 2-(2-chloro-4-[(N-methoxy-N-methylamino)carbonylamino]phenyl)methyl-5,6-dihydro-4-methyl-4-methylthio-2H-1,2-oxazin-3(4H)-one was 1.0 gram as a semi-solid. A small sample was triturated with pentane/ether to give solid product; m.p. 88°–91° C.

Analysis calcd for $C_{16}H_{22}ClN_3O_4S$: C 49.54; H 5.72; N 10.83; Found: C 49.80; H 6.11; N 10.89.

EXAMPLE 8

Synthesis of 2-(2-chloro-4-[(N-methoxy-N-methylamino)carbonylamino]phenyl)methyl-1H-2,3-benzoxazin-4(3H)-one (Compound 32)

Step A Synthesis of methyl 2-methylbenzoate as an intermediate

To a stirred solution of 40.0 grams (0.29 mole) of 2-methylbenzoic acid in 200 ml of methanol was added dropwise 20 ml of concentrated sulfuric acid. Upon completion of addition the reaction mixture was heated to reflux where it stirred for 18 hours. The reaction mixture was cooled to ambient temperature and poured into 200 ml of water. The mixture was extracted with three 100 ml portions of methylene chloride. The combined extracts were washed with two 50 ml portions of aqueous saturated sodium bicarbonate solution, then with 50 ml of water. The organic layer was dried with sodium sulfate and filtered. The filtrate was concentrated under reduced pressure to give 42.7 grams of methyl 2-methylbenzoate.

Step B Synthesis of methyl 2-bromomethylbenzoate as an intermediate

This compound was prepared in the manner of Example 6, Part A, using 42.6 grams (0.283 mole) of methyl 2-methylbenzoate, 50.4 grams (0.283 mole) of N-bromosuccinimide and 2.0 grams (0.008 mole) of benzoyl peroxide in 500 ml of carbon tetrachloride. The yield of methyl 2-bromomethylbenzoate was 64.2 grams as an oil.

Step C Synthesis of methyl 2-(phthalimidooxymethyl)benzoate as an intermediate This compound was prepared in the manner of Example 6, Part A, using 51.6 grams (0.225 mole) of methyl 2-bromomethylbenzoate, 36.7 grams (0.225 mole) of N-hydroxyphthalimide and 18.5 grams (0.225 mole) of sodium acetate in 500 ml of dimethyl sulfoxide. The yield of methyl 2-(phthalimidooxymethyl)benzoate was 52.5 grams. The compound was used without further purification.

Step D Synthesis of 1H-2,3-benzoxazin-4(3H)-one as an intermediate directly from methyl-2-(phthalimidooxymethyl)benzoate This reaction was run in the same manner as Example 6, Part B, using 52.5 grams (0.169 mole) of methyl 1-(phthalimidooxymethyl)benzoate and 17.0 grams (0.34 mole) of hydrazine hydrate in 800 ml of methanol to give 5.4 grams of 1H-2,3-benzoxazin-4(3H)-one; m.p. 123°–125° C.

Analysis calcd for $C_8H_6NO_2$: C 64.42; H 4.73; N 9.39; Found: C 64.58; H 4.49; N 9.10.

Step E Synthesis of 2-(2-chloro-4-[(N-methoxy-N-methylamino)carbonylamino]phenyl)methyl-1H-2,3-benzoxazin-4(3H)-one (Compound 32)

This compound was prepared in the manner of Example 1, Step C, using 0.5 gram (0.003 mole) of 1H-2,3-benzoxazin-4(3H)-one, 1.0 gram (0.003 mole) of 2-chloro-4-[(N-methoxy-N-methylamino)carbonylamino]phenylmethyl bromide (prepared in Example 6, Part 1, Step B), 0.5 gram (0.003 mole) of potassium carbonate, and 0.05 gram (0.0002 mole) of 1,4,7,10,13,16-hexaoxacyclooctadecane in 15 ml of acetonitrile. The yield of 2-(2-chloro-4-[(N-methoxy-N-methylamino)carbonylamino]phenyl)methyl-3,4-dihydro-1H-2,3-benzoxazin-1-one was 0.6 gram, as an oil.

nmr (CDCl$_3$/TMS) δ: 3.18 (s,3H); 3.78 (s,3H); 5.03 (s,4H); 7.0–8.2 (m,8H).

Analysis calcd for $C_{18}H_{18}ClN_3O_4$: C 57.53; H 4.83; N 11.18; Found: C 57.29; H 4.81; N 11.47.

EXAMPLE 9

Synthesis of 2-(2-chloro-4-[N-ethyl-N-(cyclopropylcarbonyl)amino]phenyl)methyl-4,4-dimethyl-3-isoxazolidinone (Compound 36)

Step A Synthesis of 1,1-dimethylethyl N-ethyl-N-(3-chloro-4-methylphenyl)carbamate as an intermediate Sodium hydride, 2.0 grams (0.05 mole) was washed repeatedly with heptane, then was stirred in 100 ml of tetrahydrofuran. To this was added 10.0 grams (0.41 mole) of 1,1-dimethylethyl(3-chloro-4-methylphenyl)carbamate (prepared in Example 4, Step A). The reaction was stirred for 5 minutes and 9.0 grams (0.083 mole) of ethyl bromide in 25 ml of tetrahydrofuran was added dropwise. Upon completion of addition the reaction mixture was stirred at ambient temperature for 16 hours. The reaction mixture was taken up in 500 ml of diethyl ether and washed with three 50 ml portions of water. The organic layer was dried with magnesium sulfate and filtered. The filtrate was concentrated under reduced pressure to give 10.8 grams of 1,1-dimethylethyl N-ethyl-N-(3-chloro-4-methylphenyl)carbamate as an oil.

Step B Synthesis of 1,1-dimethylethyl N-ethyl-N-(4-bromomethyl-3-chlorophenyl)carbamate as an intermediate This compound was prepared in the manner of Example 6, Part 1, Step A, using 10.8 grams (0.045 mole) of 1,1-dimethylethyl-N-ethyl-N-(3-chloro-4-methylphenyl)carbamate, 9.5 grams (0.053 mole) of N-bromosuccinimide, and 0.2 gram of benzoyl peroxide in 300 ml of carbon tetrachloride. The yield of 1,1-dimethylethyl N-ethyl-N-(4-bromomethyl-3-chlorophenyl)carbamate was 15.9 grams as an oil.

Step C Synthesis of 2-(2-chloro-4-[N-ethyl-N-(1,1-dimethylethoxycarbonylamino]phenyl)methyl-4,4-dimethyl-3-isoxazolidinone as an intermediate This compound was prepared in the manner of Example 1, Step C, using 15.9 grams (0.045 mole) of 1,1-dimethylethyl N-ethyl-N-(4-bromomethyl-3-chlorophenyl)- carbamate, 5.1 grams (0.044 mole) of 4,4-dimethyl-3-isoxazolidinone, 0.2 gram of 1,4,7,10,13,16-hexaoxacyclooctadecane, and 6.2 grams (0.045 mole) of potassium carbonate in 200 ml of acetonitrile. The yield of 2-(2-chloro-4-[N-ethyl-N-(1,1-dimethylethoxycarbonylamino]phenyl)methyl-4,4-dimethyl-3-isoxazolidinone was 4.9 grams.

Step D Synthesis of 2-(2-chloro-4-ethylaminophenyl)methyl-4,4-dimethyl-3-isoxazolidinone as an intermediate This compound was prepared in the manner of Example 4, Part 2, Step B, using 4.9 grams (0.013 mole) of 2-(2-chloro-4-[N-ethyl-N-(1,1-dimethylethoxycarbonylamino]phenyl)methyl-4,4-dimethyl-3-isoxazolidinone and 20.0 ml of trifluoroacetic acid in 50 ml of methylene chloride. The yield of 2-(2-chloro-4-ethylaminophenyl)methyl-4,4-dimethyl-3-isoxazolidinone was 2.7 grams as a solid; m.p. 135°–138° C.

Step E Synthesis of 2-(2-chloro-4-[N-ethyl-N-(cyclopropylcarbonyl)amino]phenyl)methyl-4,4-dimethyl-3-isoxazolidinone (Compound 36)

This compound was prepared in the manner of Example 5, using 1.1 grams (0.004 mole) of 2-(2-chloro-4-ethylaminophenyl)methyl-4,4-dimethyl-3-isoxazolidinone, 0.4 ml of cyclopropanecarboxylic acid chloride, and 0.4 ml of triethylamine in 50 ml of tetrahydrofuran. The yield of 2-(2-chloro-4-[N-ethyl-N-(cyclopropylcarbonyl)amino]phenyl)methyl-4,4-dimethyl-3-isoxazolidinone was 0.99 gram as an oil.

nmr (CDCl$_3$/TMS) δ: 0.5–1.15 (m,8H); 1.34 (s,6H); 3.58–4.00 (q,2H); 4.08 (s,2H); 4.84 (s,2H); 7.10–7.58 (m,3H).

Analysis calcd for C$_{18}$H$_{23}$ClN$_2$O$_3$: C 61.62; H 6.61; N 7.98; Found: C 61.90; H 6.52; N 7.89.

The intermediate 2-(4-amino- or 5-amino substituted phenyl)methyl-4,4-dimethyl-3-isoxazolidinone, the intermediate used in Examples 2, Step B and 4 Step D, may also be prepared by reacting an appropriately substituted 4 or 5 nitrobenzyl bromide with the 3-isoxazolidinone or 3-oxazinone and reducing the nitro group, or by reacting an appropriately substituted benzyl bromide with the 3-isoxazolidinone or 3-oxazinone, nitrating the open 4 or 5 position of the substituted phenyl ring, then reducing the resulting nitro group to an amino group.

The test species used in demonstrating the herbicidal activity of the compounds were limabean (*Phaseolus limensis*), field corn (*Zea mays* L.), soybean (*Glycine max*), wheat (*Triticum aestivum*), barnyardgrass (*Echinochloa crus galli*), johnsongrass (*Sorghum halepense*), pitted morningglory (*Ipomoea lacunosa*), velvetleaf (*Abutilon theophrasti*), field bindweed (*Convolvulus arvenia*), and green foxtail (*Setaria viridis*).

For preemergence tests, seeds of the test species were planted in flats containing approximately a 5-cm depth of sandy loam soil. Prior to seeding, the rows were marked by pressing a wooden template onto the soil surface. After sowing, a fungicidal treatment was sprinkled on the seed bed, and a thin layer of soil (approximately 1.0 cm) was applied to the surface of the flat. The spray solutions containing the compounds of the invention were then applied directly to the soil as aqueous acetone solutions at rates equivalent to 8.00 kilograms active ingredient per hectare or submultiples thereof (4.00 kg/ha, 2.00 kg/ha, 1.00 kg/ha, etc.) and at a volume equivalent to 750 liters/hectare.

The test plants were maintained in a greenhouse and watered regularly on the soil surface for 13 days, at which time phytotoxicity was observed. The number of dead plants, including those not expected to survive, and living plants were determined and percent kill (K) was calculated. A vigor rating (V) was also recorded based on the following observations:

| Rating | Description |
| --- | --- |
| 5 | Plants normal |
| 4 | Slight injury |
| 3 | Moderate injury |
| 2 | Moderate to severe injury |
| 1 | Severe injury |
| 0 | Dead plant |

In some instances the Vigor and K ratings were combined into a single result expressed as "percent control".

The results reported in Table 2, illustrate the preemergent herbicidal activity of the invention.

For postemergence tests seeds of test plants were planted in flats as in the preemergence tests then placed in a greenhouse for an 8 to 10 day growing period, at which time spray solutions containing the compounds of the invention were applied to the plants at a rate equivalent to 8 kg active ingredient per hectare or a submultiple thereof. The treated plants were then placed in the greenhouse and watered regularly for 13 days, at which time phytotoxicity was observed in the same manner as for the preemergence tests. The results reported in Table 3 illustrate the postemergence herbicidal activity of the compounds of the invention.

For application the herbicidal compounds of this invention will not ordinarily be applied in undiluted form, but will be diluted or extended with an agriculturally acceptable, relatively inert material, here called a carrier, which may be liquid or solid. The compounds may be used as broad spectrum herbicides or as selective herbicides for undesired vegetation which is commonly found in crops such as corn and sorghum, and to a lesser extent wheat and rice, by adjusting the concentration and application rate.

Thus, the compounds of this invention may be utilized in diverse formulations prepared from agricultural adjuvants and agricultural carriers to give the herbicidal compositions contemplated herein. The herbicidal compositions contain between about 0.01% and 95% active ingredient together with between about 4% and 98.5% agriculturally acceptable carrier and between about 1% and 15% surface active agent by weight. As is well-known in the art, the formulation and mode of application of a toxicant may affect the activity of the material in a given application. Thus, a compound of this invention may be formulated as an emulsifiable concentrate, as a granule of relatively large particle size, as a wettable powder, as a solution, or as any of several other known types of formulations, depending on the desired mode of application.

Emulsifiable concentrates are homogeneous liquid or paste compositions dispersible in water or other dispersant, and may consist entirely of a compound of this invention with a liquid or solid emulsifying agent, or may also contain an agriculturally acceptable liquid carrier, such as xylene, heavy aromatic naphthas, isophorone and other non-volatile organic solvents. For example, a useful emulsifiable concentrate formulation, designated "4EC" because it contains four pounds of active ingredient per gallon of concentrate (0.479 kg/liter), will contain 53.01 parts of active ingredient, 6.0 parts of a blend of alkylnaphthalenesulfonate and polyoxyethylene ethers as emulsifiers, 1.0 part of epoxidized soybean oil as stabilizer, and as solvent 39.99 parts of petroleum distillate having a high flash-point.

Granular formulations are particularly useful for aerial distribution. Useful granular formulations may be of several types. Impregnated granules are those wherein the active ingredient is applied to large particles of an absorbent carrier, such as an attapulgite or kaolin clay, corncobs, expanded mica, normally in the form of a solution in a solvent. Surface-coated granules may be produced by spraying the molten active ingredient onto the surface of a generally nonabsorbent particle or by spraying on a solution of active ingredient in a solvent. The core may be water-soluble such as a prilled fertilizer, or insoluble such as sand, marble chips or coarse talc. Particularly useful is a granule wherein a wettable powder is applied as a surface coating to sand or other insoluble particle such that the wettable powder may be dispersed on contact of the granule with moisture. Granules may be produced by agglomeration of dusts or powders by compaction rollers, by extrusion through a die or by use of granulating disc. Granular formulations may vary widely in concentration, with useful formulations containing as little as 0.5% or as much as 95% of active ingredient.

Wettable powders, also useful formulations for pre-emergence herbicides, are in the form of finely divided particles which disperse readily in water or other dispersants. The wettable powder is ultimately applied to the soil as a finely divided dry material or as an emulsion in water or other liquid. Typical carriers for wettable powders include fuller's earth, kaolin clays, silicas and other highly absorbent, readily wet inorganic diluents. Wettable powders normally are prepared to contain about 5% to 80% of active ingredient, depending on the absorbability of the active ingredient and on the absorbency of the carrier, and usually also contain a small amount of a wetting, dispersing or emulsifying agent to facilitate dispersion.

Typical wetting, dispersing or emulsifying agents used in agricultural formulations include, for example, the alkyl and alkylaryl sulfonates and sulfates and their sodium salts; polyethylene oxides; sulfonated oils, fatty acid esters of polyhydric alcohols; and other types of surface active agents, many of which are available in commerce.

The surface-active agent, when used, normally comprises from 1% to 15% by weight of the herbicidal compositions.

These formulations may be applied without further dilution or as dilute solutions, emulsions or suspensions in water or other suitable diluent. The compositions may be applied to the area wherein control is desired by spraying onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compounds of this invention may be formulated and/or applied with insecticides, fungicides, nematicides, plant growth regulators, fertilizers, and other agricultural chemicals. In applying the active compounds of this invention, whether formulated alone or with other agricultural chemicals, an effective amount and concentration of active ingredient are of course employed. The amount constituting an effective amount is variable, depending on a number of factors such as the type of soil, the expected pattern of rainfall or irrigation, the plant species to be controlled, and the crop, if any, to be grown. Generally, a uniform application of between 0.1 and 9 kilograms per hectare will be employed, for example, 0.25 to 4.00 kilograms per hectare.

It is apparent that various modifications may be made in the formulation and application of the novel compounds of this invention, without departing from the inventive concept herein, as defined in the following claims.

TABLE 1

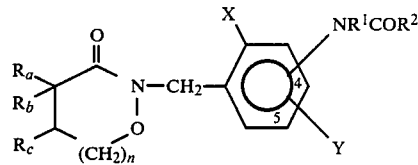

| CPD No. | n | X | $R^1$ | $R^2$ | Comment[a] | M.P. (°C.) |
|---|---|---|---|---|---|---|
| 1 | 0 | Cl | H | $CH_3$ | — | 199–200 |
| 2 | 0 | Cl | H | $C_2H_5$ | — | 151–153 |
| 3 | 0 | Cl | H | $C_3H_7$ | — | 138–140 |
| 4 | 0 | Cl | H | $i-C_3H_7$ | — | 168–170 |
| 5 | 0 | Cl | H | $n-C_4H_9$ | — | 110–115 |
| 6 | 0 | Cl | H | $CH(CH_3)C_2H_5$ | — | 129–131 |
| 7 | 0 | Cl | H | $t-C_4H_9$ | — | 135–137 |
| 8 | 0 | Cl | H | $C(CH_3)_2C_2H_5$ | — | 118–119 |
| 9 | 0 | Cl | H | $CH(CH_3)C_4H_9$ | — | 120–126 |
| 10 | 0 | Cl | H | $CCl_2CH_3$ | — | 98–102 |
| 11 | 0 | Cl | H | $C(CH_3)_2CH_2Cl$ | — | 150–152 |
| 12 | 0 | Cl | H | cyclopropyl | — | Ex. 5 |
| 13 | 0 | Cl | H | benzyl | — | 125–127 |
| 14 | 0 | Cl | H | $OCH_3$ | — | Ex. 1(C) |
| 15 | 0 | Cl | H | $OC_2H_5$ | — | Ex. 2(A) |
| 16 | 0 | Cl | H | $O(CH_2)_3CH_2Cl$ | — | 106–108 |
| 17 | 0 | H | H | $NHCH_3$ | — | 144–146 |
| 18 | 0 | H | H | $N(CH_3)_2$ | — | 118–121 |
| 19 | 0 | Cl | H | $NHCH_3$ | — | Ex. 2(C) |
| 20 | 0 | Cl | H | $N(CH_3)_2$ | — | Ex. 4(E) |
| 21 | 0 | Cl | H | $N(CH_3)OCH_3$ | — | Ex. 3(B) |
| 22 | 0 | Cl | H | $N(CH_3)CH_2Ph$. | — | 115–117 |
| 23 | 0 | F | H | $N(CH_3)_2$ | — | 120–123 |
| 24 | 0 | F | H | $N(CH_3)OCH_3$ | — | 102–106 |
| 25 | 0 | Cl | H | $N(CH_3)_2$ | $R_a, R_b = H$ | 126–129 |
| 26 | 0 | Cl | H | $N(CH_3)_2$ | $R_c = CH_3$ | 118–121 |
| 27 | 0 | Cl | H | $N(CH_3)_2$ | $R_c = $ phenyl | 57–67 |
| 28 | 1 | Cl | H | $N(CH_3)_2$ | — | 108–110 |
| 29 | 1 | Cl | H | $N(CH_3)OCH_3$ | — | Ex. 6(C) |
| 30 | 1 | Cl | H | $N(CH_3)_2$ | $R_b = SCH_3$ | d |
| 31 | 1 | Cl | H | $N(CH_3)OCH_3$ | $R_b = SCH_3$ | Ex. 7(F) |
| 32 | 1 | Cl | H | $N(CH_3)OCH_3$ | $R_a + R_b + R_c$ = phenyl | Ex. 8(E) |
| 33 | 0 | Cl | $CH_3$ | $CH_3$ | — | 105–107 |
| 34 | 0 | Cl | $CH_3$ | $C(CH_3)_3$ | — | d |
| 35 | 0 | Cl | $CH_3$ | cyclopropyl- | — | 85–88 |
| 36 | 0 | Cl | $C_2H_5$ | cyclopropyl- | — | Ex. 9(E) |
| 37 | 0 | Cl | $n-C_3H_7$ | cyclopropyl- | — | d |
| 38 | 0 | Cl | $i-C_3H_7$ | cyclopropyl- | — | d |
| 39 | 0 | Cl | $CH_3$ | $OC(CH_3)_3$ | — | d |
| 40 | 0 | Cl | $C_2H_5$ | $OC(CH_3)_3$ | — | d |
| 41 | 0 | Cl | H | $N(CH_3)OCH_3$ | c | 81–84 |
| 42 | 0 | Cl | H | $N(CH_3)_2$ | c | 166–167 |
| 43 | 0 | F | H | $C(CH_3)_3$ | — | 157–158 |
| 44 | 0 | F | H | cyclopropyl | — | 170–172 |
| 45 | 0 | F | H | 1-methylcyclo-propyl | — | 128–129 |
| 46 | 0 | Cl | H | 1-methylcyclo-propyl | — | 107–108 |
| 47 | 0 | Br | H | $C(CH_3)_3$ | — | 131–132 |
| 48 | 0 | Cl | H | $C(CH_3)_3$ | Y = 5-F | d |

TABLE 1-continued

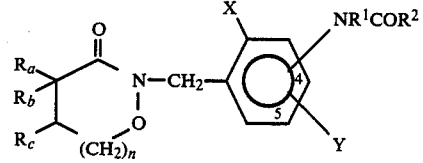

| CPD No. | n | X | R¹ | R² | Comment[a] | M.P. (°C.) |
|---|---|---|---|---|---|---|
| 49 | 0 | Cl | H | N(CH₃)₂ | Y = 5-F | d |
| 50 | 0 | Cl | H | C(CH₃)₃ | c | 154–155 |
| 51 | 0 | Cl | H | OC(CH₃)₃ | Y = 4-Cl[c] | d |

[a]$R_a$ and $R_b$ are both methyl, $R_c$ = H, Y = H, and NR¹COR² is at position 4 unless otherwise specified.
[b]Melting point or reference to Example number and step where prepared and characterized.
[c]NR¹COR² in position 5.
[d]nmr consistent with assigned structure.

TABLE 2

| | Preemergence Screen | | | | | | | | | | | | | | | | |
|---|---|---|---|---|---|---|---|---|---|---|---|---|---|---|---|---|---|
| | BGr[a] | | F.Bwd[b] | | Corn | | GFx[c] | | Jgr[d] | | Lbn[e] | | Mgl[f] | | Sbn[g] | | Vtlf[h] | | Wht[i] |
| Cmpd | V | K | V | K | V | K | V | K | V | K | V | K | V | K | V | K | V | K | V | K |
| 1 | 4 | 10 | 5 | 0 | — | — | 4 | 0 | — | — | 3 | 0 | 4 | 0 | 3 | 0 | 4 | 0 | — | — |
| 2 | 0 | 100 | 2 | 95 | 4 | 30 | 3 | 90 | — | — | — | — | — | — | 3 | 20 | 0 | 100 | 4 | 10 |
| 3 | 5 | 0 | 5 | 0 | 5 | 0 | 4 | 0 | — | — | 3 | 0 | — | — | 2 | 40 | 3 | 0 | 5 | 0 |
| 4 | 0 | 100 | 3 | 90 | 4 | 0 | 0 | 100 | — | — | 3 | 60 | 2 | 100 | 3 | 0 | 0 | 100 | 2 | 90 |
| 5 | 4 | 0 | 4 | 40 | 5 | 0 | 2 | 90 | 4 | 0 | 5 | 0 | 3 | 80 | 3 | 0 | 0 | 100 | 5 | 0 |
| 6(j) | 0 | 100 | 3 | 95 | 5 | 0 | 3 | 95 | 4 | 20 | 3 | 20 | 0 | 100 | 4 | 0 | 0 | 100 | 4 | 20 |
| 7 | 2 | 0 | 3 | 30 | 4 | 0 | 0 | 100 | — | — | 2 | 0 | — | — | 2 | 0 | 0 | 100 | 3 | 20 |
| 8 | 4 | 20 | 4 | 20 | 5 | 0 | 4 | 30 | 5 | 0 | 3 | 30 | 0 | 100 | 3 | 0 | 0 | 100 | 3 | 0 |
| 9 | 4 | 0 | 4 | 0 | 4 | 30 | 4 | 0 | 4 | 0 | 4 | 40 | 3 | 30 | 3 | 20 | 4 | 0 | 4 | 0 |
| 10 | 4 | 0 | 5 | 0 | 4 | 0 | 3 | 40 | 3 | 20 | 3 | 50 | 4 | 0 | 3 | 30 | 4 | 0 | 3 | 20 |
| 11 | 4 | 0 | 4 | 10 | 5 | 0 | 4 | 0 | 5 | 0 | 3 | 20 | 0 | 100 | 3 | 0 | 0 | 100 | 3 | 50 |
| 12 | 3 | 50 | 0 | 100 | 4 | 0 | 3 | 50 | 4 | 0 | 1 | 95 | 0 | 100 | 3 | 0 | 0 | 100 | 2 | 0 |
| 13 | 3 | 90 | 5 | 0 | 5 | 0 | 4 | 50 | 4 | 0 | 4 | 50 | 0 | 100 | 4 | 0 | 0 | 100 | 4 | 0 |
| 14 | 0 | 100 | 4 | 30 | — | — | 0 | 100 | 0 | 100 | 3 | 20 | 0 | 100 | 3 | 0 | 0 | 100 | — | — |
| 15 | 3 | 0 | 4 | 20 | — | — | 4 | 30 | 2 | 0 | 5 | 0 | 4 | 0 | 5 | 0 | 4 | 95 | — | — |
| 16 | 4 | 0 | 5 | 0 | 5 | 0 | 4 | 0 | 4 | 0 | 5 | 0 | 5 | 0 | 5 | 0 | 4 | 40 | 4 | 0 |
| 17 | 2 | 90 | 2 | 90 | 2 | 70 | 2 | 90 | — | — | — | — | — | — | 1 | 90 | 0 | 100 | 0 | 100 |
| 18 | 0 | 100 | 0 | 100 | 0 | 100 | 0 | 100 | — | — | — | — | — | — | 0 | 100 | 0 | 100 | 0 | 100 |
| 19 | 0 | 100 | 0 | 100 | — | — | 2 | 95 | 0 | 100 | 0 | 100 | 0 | 100 | 0 | 100 | 0 | 100 | — | — |
| 20 | 0 | 100 | 0 | 100 | 0 | 100 | 0 | 100 | — | — | — | — | — | — | — | — | 0 | 100 | 0 | 100 |
| 21[j] | 0 | 100 | 0 | 100 | 2 | 98 | 0 | 100 | 0 | 100 | — | — | 0 | 100 | 2 | 98 | 0 | 100 | 0 | 100 |
| 22 | 4 | 0 | 5 | 0 | 5 | 0 | 3 | 60 | — | — | 5 | 0 | — | — | 5 | 0 | 4 | 90 | 5 | 0 |
| 23[k] | 0 | 100 | 0 | 100 | 0 | 100 | 0 | 100 | 0 | 100 | — | — | 0 | 100 | 0 | 100 | 0 | 100 | 0 | 100 |
| 24[k] | 0 | 100 | 0 | 100 | 4 | 60 | 0 | 100 | 0 | 100 | — | — | 0 | 100 | 0 | 100 | 0 | 100 | 0 | 100 |
| 25 | 3 | 0 | 3 | 90 | 3 | 30 | 3 | 95 | — | — | 3 | 0 | — | — | 4 | 30 | 3 | 95 | 3 | 30 |
| 26 | 0 | 100 | 0 | 100 | 0 | 100 | 0 | 100 | — | — | — | — | — | — | 2 | 85 | 0 | 100 | 0 | 100 |
| 27 | 3 | 70 | 3 | 60 | 0 | 100 | 2 | 95 | 4 | 0 | 4 | 0 | 0 | 100 | 3 | 0 | 0 | 100 | 3 | 75 |
| 28[j] | 1 | 98 | 0 | 100 | 3 | 70 | 0 | 100 | 0 | 100 | — | — | 0 | 100 | 0 | 100 | 0 | 100 | — | — |
| 29 | 2 | 80 | 0 | 100 | 0 | 100 | 2 | 70 | 3 | 30 | 2 | 80 | 0 | 100 | 2 | 80 | 2 | 90 | 3 | 20 |
| 30 | 0 | 100 | 0 | 100 | 0 | 100 | 0 | 100 | 3 | 95 | — | — | 0 | 100 | 0 | 100 | 0 | 100 | 0 | 100 |
| 31 | 3 | 95 | 3 | 95 | 0 | 100 | 0 | 100 | 3 | 95 | — | — | 0 | 100 | 0 | 100 | 0 | 100 | 0 | 100 |
| 32 | Inactive | | | | | | | | | | | | | | | | | | | |
| 33 | 0 | 100 | 3 | 50 | 2 | 20 | 0 | 100 | 3 | 20 | 2 | 20 | 2 | 30 | 2 | 0 | 3 | 90 | 2 | 90 |
| 34 | 0 | 100 | 3 | 30 | 2 | 30 | 3 | 40 | 3 | 20 | 2 | 0 | 2 | 40 | 2 | 0 | 3 | 95 | 2 | 90 |
| 35 | 0 | 100 | 0 | 100 | 0 | 100 | 0 | 100 | 0 | 100 | 2 | 80 | 2 | 80 | 2 | 30 | 0 | 100 | 0 | 100 |
| 36 | 0 | 100 | 2 | 80 | 0 | 100 | 0 | 100 | 3 | 70 | 0 | 100 | 2 | 95 | 2 | 0 | 2 | 95 | 0 | 100 |
| 37 | 3 | 70 | 4 | 0 | 2 | 0 | 4 | 80 | 4 | 0 | 4 | 0 | 2 | 95 | 3 | 0 | 0 | 100 | 2 | 80 |
| 38 | 3 | 20 | 4 | 20 | 2 | 0 | 4 | 0 | 4 | 0 | 3 | 0 | 3 | 95 | 3 | 0 | 4 | 0 | 4 | 0 |
| 39 | 0 | 100 | 4 | 20 | 3 | 30 | 4 | 90 | 2 | 50 | 5 | 0 | 5 | 0 | 5 | 0 | 5 | 0 | 4 | 0 |
| | 0 | 100 | 5 | 0 | 2 | 30 | 3 | 50 | 2 | 80 | 4 | 0 | 5 | 0 | 5 | 0 | 4 | 0 | 3 | 0 |
| 40 | 0 | 100 | 4 | 0 | 0 | 100 | 4 | 30 | 3 | 0 | 4 | 0 | 4 | 0 | 4 | 0 | 3 | 20 | 4 | 0 |
| 41 | 2 | 95 | 0 | 100 | 2 | 30 | 0 | 100 | 0 | 100 | — | — | 0 | 100 | 2 | 0 | 0 | 100 | 3 | 10 |
| 42 | 0 | 100 | 0 | 100 | 2 | 70 | 0 | 100 | 0 | 100 | — | — | 0 | 100 | 2 | 0 | 0 | 100 | 2 | 85 |
| 43[l,m] | | 50 | | 100 | | 60 | | 90 | | 50 | | — | | 90 | | 100 | | 100 | | 100 |
| 44[l,m] | | 100 | | 100 | | 100 | | 100 | | 90 | | — | | 100 | | 90 | | 100 | | 100 |
| 45[l,m] | | 100 | | 100 | | 70 | | 100 | | 100 | | — | | 100 | | 100 | | 100 | | 100 |
| 46[l,m] | | 100 | | 100 | | 100 | | 90 | | 90 | | — | | 100 | | 90 | | 90 | | 100 |
| 47[j,m] | | 60 | | 60 | | 40 | | 70 | | 50 | | — | | 100 | | 90 | | 100 | | 90 |
| 48[l,m] | | 90 | | 90 | | 20 | | 100 | | 90 | | — | | 100 | | 70 | | 90 | | 90 |
| 49[j,m] | | 100 | | 100 | | 90 | | 100 | | 100 | | — | | 100 | | 100 | | 100 | | 90 |
| 50 | 3 | 90 | 4 | 0 | 5 | 0 | 4 | 80 | 5 | 0 | — | — | 3 | 0 | 4 | 0 | 5 | 0 | 5 | 0 |
| 51 | 0 | 100 | 4 | 0 | 4 | 0 | 0 | 100 | 2 | 60 | — | — | 3 | 0 | 5 | 0 | 5 | 0 | 5 | 0 |

[a]BGr = barnyardgrass.
[b]Bwd = field bindweed.
[c]GFx = green foxtail.
[d]Jgr = johnsongrass.
[e]Lbn = limabean.
[f]Mgl = morningglory, spp.
[g]Sbn = soybean.
[h]Vtlf = velvetleaf.
[i]Wht = wheat.
[j]Rate = 2 kg/ha
[k]Rate = 1 kg/ha
[l]Rate = 4 kg/ha
[m]Vigor V and percent kill (K) combined to form percent control.

TABLE 3*

| | BGr[a] | | F.Bwd[b] | | Corn | | GFx[c] | | Jgr[d] | | Lbn[e] | | Mgl[f] | | Sbn[g] | | Vtlf[h] | | Wht[i] | |
|---|---|---|---|---|---|---|---|---|---|---|---|---|---|---|---|---|---|---|---|---|
| Cmpd | V | K | V | K | V | K | V | K | V | K | V | K | V | K | V | K | V | K | V | K |
| 1 | 4 | 0 | 4 | 0 | 5 | 0 | 4 | 0 | — | — | 5 | 0 | — | — | 4 | 0 | 3 | 0 | 4 | 0 |
| 2 | 0 | 100 | 0 | 100 | 0 | 100 | 0 | 100 | — | — | — | — | — | — | 3 | 20 | 0 | 100 | 4 | 0 |
| 3 | 4 | 0 | 4 | 0 | 5 | 0 | 3 | 0 | | | 3 | 0 | — | — | 3 | 0 | 3 | 95 | 4 | 0 |
| 4 | 3 | 95 | 4 | 0 | 5 | 0 | 3 | 90 | — | — | 2 | 0 | 3 | 20 | 0 | 100 | 0 | 100 | 3 | 95 |
| 5 | 5 | 0 | 3 | 95 | 4 | 0 | 0 | 100 | 3 | 30 | 2 | 85 | 4 | 95 | 3 | 10 | 0 | 100 | 0 | 100 |
| 6 | 4 | 20 | 4 | 0 | 5 | 0 | 0 | 100 | 4 | 20 | 3 | 80 | 3 | 20 | 3 | 80 | 0 | 100 | 3 | 50 |
| 7 | 0 | 100 | 3 | 90 | 4 | 0 | 0 | 100 | — | — | 0 | 100 | — | — | 0 | 100 | 0 | 100 | 0 | 100 |
| 8 | 4 | 0 | 4 | 0 | 4 | 0 | 4 | 0 | 5 | 0 | 2 | 0 | 3 | 0 | 2 | 0 | 0 | 100 | 3 | 0 |
| 9 | 4 | 80 | 0 | 100 | 5 | 0 | 1 | 95 | 4 | 0 | 3 | 20 | 4 | 70 | 4 | 50 | 0 | 100 | 3 | 95 |
| 10 | 4 | 0 | 5 | 0 | 3 | 0 | 3 | 95 | 4 | 0 | 3 | 0 | 5 | 0 | 3 | 0 | 0 | 100 | 3 | 0 |
| 11 | 4 | 0 | 4 | 0 | 5 | 0 | 4 | 30 | 4 | 0 | 2 | 20 | 4 | 0 | 2 | 20 | 2 | 20 | 4 | 0 |
| 12 | 3 | 50 | 0 | 100 | 4 | 0 | 0 | 100 | 4 | 20 | 0 | 100 | 4 | 60 | 4 | 80 | 0 | 100 | 0 | 100 |
| 13 | 3 | 0 | 3 | 20 | 4 | 30 | 0 | 100 | 4 | 0 | 1 | 0 | 3 | 60 | 0 | 100 | 0 | 100 | 3 | 0 |
| 14 | 3 | 80 | 3 | 20 | 5 | 0 | 4 | 95 | — | — | 4 | 0 | — | — | 3 | 30 | 0 | 100 | 3 | 20 |
| 15 | 5 | 0 | 4 | 30 | 5 | 0 | 5 | 0 | — | — | 5 | 0 | — | — | 5 | 0 | 4 | 20 | 5 | 0 |
| 16 | 4 | 30 | 0 | 100 | 5 | 0 | 0 | 100 | 4 | 0 | 3 | 0 | 4 | 60 | 4 | 0 | 0 | 100 | 3 | 40 |
| 17 | 2 | 70 | 4 | 0 | 4 | 0 | 3 | 40 | — | — | — | — | — | — | 1 | 95 | 0 | 100 | 1 | 95 |
| 18 | 0 | 100 | 0 | 100 | 0 | 100 | 3 | 50 | — | — | — | — | — | — | 0 | 100 | 0 | 100 | 0 | 100 |
| 19 | 0 | 100 | 0 | 100 | 0 | 100 | 0 | 100 | — | — | 0 | 100 | — | — | 0 | 100 | 0 | 100 | 0 | 100 |
| 20 | 0 | 100 | 0 | 100 | 0 | 100 | 0 | 100 | — | — | — | — | — | — | — | — | 0 | 100 | 0 | 100 |
| 21 | 0 | 100 | 3 | 30 | 0 | 100 | 0 | 100 | — | — | 2 | 0 | — | — | 0 | 100 | 0 | 100 | 2 | 80 |
| 22 | 4 | 0 | 4 | 0 | 4 | 0 | 4 | 0 | | | 3 | 40 | | | 3 | 40 | 0 | 100 | 4 | 0 |
| 23 | 4 | 0 | 0 | 100 | 0 | 100 | 0 | 100 | 4 | 10 | — | — | 0 | 100 | 0 | 100 | 0 | 100 | 0 | 100 |
| 24 | 3 | 40 | 0 | 100 | 0 | 100 | 0 | 100 | 4 | 60 | — | — | 0 | 100 | 0 | 100 | 0 | 100 | 0 | 100 |
| 25 | 0 | 100 | 3 | 10 | 4 | 30 | 3 | 95 | — | — | 2 | 0 | — | — | 0 | 100 | 0 | 100 | 0 | 100 |
| 26 | 0 | 100 | 0 | 100 | 0 | 100 | 0 | 100 | — | — | — | — | — | — | 0 | 100 | 0 | 100 | 0 | 100 |
| 27 | — | — | 0 | 100 | 4 | 0 | 0 | 100 | 3 | 40 | 2 | 0 | 0 | 100 | 0 | 100 | 0 | 100 | 0 | 100 |
| 28 | 0 | 100 | 0 | 100 | 0 | 100 | 0 | 100 | — | — | 2 | 30 | — | — | 0 | 100 | 0 | 100 | 0 | 100 |
| 29 | — | — | 0 | 100 | 2 | 30 | 0 | 100 | 0 | 100 | 0 | 100 | 0 | 100 | 0 | 100 | 0 | 100 | 0 | 100 |
| 30 | 4 | 50 | 0 | 100 | 0 | 100 | 0 | 100 | 3 | 70 | — | — | 0 | 100 | 0 | 100 | 0 | 100 | 0 | 100 |
| 31 | 3 | 20 | 0 | 100 | 4 | 0 | 0 | 100 | 3 | 20 | — | — | 0 | 100 | 0 | 100 | 0 | 100 | 0 | 100 |
| 32 | 4 | 70 | 0 | 100 | 5 | 0 | 0 | 100 | 4 | 30 | — | — | 0 | 100 | 0 | 100 | 0 | 100 | 4 | 10 |
| 33 | 3 | 0 | 3 | 90 | 4 | 0 | 3 | 30 | 2 | 40 | 3 | 0 | 3 | 50 | 3 | 0 | 3 | 90 | 4 | 0 |
| 34 | 3 | 10 | 2 | 95 | 4 | 0 | 3 | 80 | 4 | 80 | 3 | 40 | 3 | 70 | 4 | 20 | 0 | 100 | 3 | 40 |
| 35 | 0 | 100 | 0 | 100 | 0 | 100 | 0 | 100 | 0 | 100 | 0 | 100 | 3 | 95 | 0 | 100 | 0 | 100 | 0 | 100 |
| 36 | 3 | 85 | 0 | 100 | 2 | 0 | 3 | 95 | 4 | 0 | 0 | 100 | 0 | 100 | 3 | 60 | 0 | 100 | 0 | 100 |
| 37 | 4 | 0 | 4 | 40 | 4 | 0 | 3 | 90 | 3 | 50 | 4 | 0 | 4 | 0 | 3 | 0 | 4 | 40 | 3 | 0 |
| 38 | 3 | 30 | 4 | 20 | 4 | 0 | 2 | 80 | 3 | 20 | 4 | 0 | 3 | 10 | 3 | 0 | 3 | 20 | 4 | 0 |
| 39 | 3 | 0 | 4 | 0 | 4 | 0 | 4 | 0 | 3 | 0 | 4 | 0 | 4 | 0 | 4 | 0 | 4 | 0 | 4 | 0 |
| 40 | 2 | 70 | 4 | 0 | 3 | 0 | 4 | 0 | 2 | 95 | 3 | 0 | 4 | 0 | 3 | 0 | 3 | 40 | 3 | 0 |
| 41 | 3 | 10 | 0 | 100 | 4 | 35 | 0 | 100 | 3 | 15 | — | — | 0 | 100 | 4 | 0 | — | — | 4 | 0 |
| 42 | 0 | 100 | 0 | 100 | 4 | 35 | 0 | 100 | 0 | 100 | — | — | 0 | 100 | 2 | 50 | — | — | 0 | 100 |
| 43[l,m] | | 30 | | 70 | | 10 | | 70 | | 30 | | — | | 80 | | 100 | | 100 | | 60 |
| 44[l,m] | | 100 | | 90 | | 100 | | 100 | | 100 | | — | | 80 | | 100 | | 100 | | 100 |
| 45[l,m] | | 100 | | 100 | | 100 | | 100 | | 90 | | — | | 90 | | 100 | | 100 | | 100 |
| 46[l,m] | | 90 | | 90 | | 100 | | 100 | | 90 | | — | | 90 | | 100 | | 100 | | 100 |
| 47[l,m] | | 0 | | 80 | | 0 | | 80 | | 30 | | — | | 20 | | 80 | | 100 | | 90 |
| 48[l,m] | | 100 | | 100 | | 40 | | 100 | | 40 | | — | | 100 | | 100 | | 100 | | 100 |
| 49[j,m] | | 100 | | 100 | | 100 | | 100 | | 100 | | — | | 100 | | 100 | | 100 | | 100 |

*See footnotes to Table 2.

What is claimed is:

1. A compound of the formula

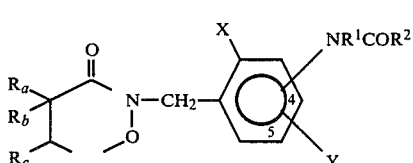

in which n is zero or one; $NR^1COR^2$ is in one of positions 4 and 5;

$R_a$ is hydrogen or alkyl of 1 to 3 carbon atoms;

$R_b$ is hydrogen, alkyl of 1 to 3 carbon atoms, or methylthio;

$R_c$ is hydrogen, alkyl of 1 to 3 carbon atoms, or phenyl; or $R_a$, $R_b$ and $R_c$ taken with the carbon atoms at positions 4' and 5' form a benzene ring;

X is hydrogen or halogen;

Y is hydrogen or halogen at the other of positions 4 and 5;

$R^1$ is hydrogen, or alkyl of 1 to 4 carbon atoms;

$R^2$ is alkyl of 1 to 6 carbon atoms, haloalkyl of 2 to 4 carbon atoms, cyclopropyl, methylcyclopropyl, benzyl, alkoxy of 1 to 2 carbon atoms, t-butyloxy when $R^1$ or Y is other than hydrogen, haloalkoxy of 3 or 4 carbon atoms, or $-NR^3R^4$;

$R^3$ is methyl; and $R^4$ is hydrogen, methyl, methoxy or benzyl.

2. The compound of claim 1 in which

A.
 n is zero;
 $R_a$ and $R_b$ are both hydrogen or alkyl of 1 to 3 carbon atoms; and
 $R_c$ is hydrogen, alkyl of 1 to 3 carbon atoms, or phenyl; or B.
 n is 1;
 $R_a$ is alkyl of 1 to 3 carbon atoms;
 $R_b$ is alkyl of 1 to 3 carbon atoms or methylthio;

$R_c$ is hydrogen; or $R_a$, $R_b$ and $R_c$ together with the carbons at positions 4' and 5' form a benzene ring;

$R^1$ is hydrogen;

$R^2$ is $NR^3R^4$;

$R^3$ is methyl; and $R^4$ is methyl or methoxy.

3. The compounds of claim 1 in which;

n is zero, $NR^1COR^2$ is at position 4;

$R_a$ and $R_b$ are both methyl;

$R_c$ is hydrogen;

X is chloro or fluoro;

Y is hydrogen or 5-fluoro;

$R^1$ is hydrogen; and $R^2$ is $N(CH_3)R^5$ in which $R^5$ is methyl or methoxy.

4. A compound of the formula

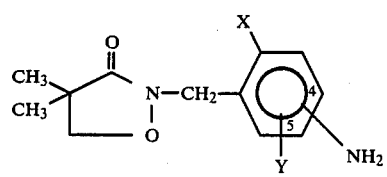

in which X is halogen, Y is hydrogen, chloro, or fluoro, one of Y and $NH_2$ is in position 5 and the other of Y and $NH_2$ is in position 4.

5. A herbicidal composition comprising a herbicidally effective amount of the compound of claim 1 in admixture with an agriculturally acceptable carrier, diluent, or adjuvant.

6. A herbicidal composition comprising a herbicidally effective amount of the compound of claim 2 in admixture with an agriculturally acceptable carrier, diluent, or adjuvant.

7. A herbicidal composition comprising a herbicidally effective amount of the compound of claim 3 in admixture with an agriculturally acceptable carrier, diluent, or adjuvant.

8. A method for controlling undesired vegetation comprising applying to the locus where control is desired an herbicidally effective amount of the compound of claim 1.

9. A method for controlling undesired vegetation comprising applying to the locus where control is desired an herbicidally effective amount of the compound of claim 2.

10. A method for controlling undesired vegetation comprising applying to the locus where control is desired an herbicidally effective amount of the compound of claim 3.

* * * * *